United States Patent [19]
Nissen et al.

[11] Patent Number: 6,031,000
[45] Date of Patent: Feb. 29, 2000

[54] COMPOSITION COMPRISING β-HYDROXY-β-METHYLBUTYRIC ACID AND AT LEAST ONE AMINO ACID AND METHODS OF USE

[75] Inventors: Steven L. Nissen, Ames, Iowa; Naji M. Abumrad, Old Field, N.Y.

[73] Assignee: Iowa State University Research Foundation, Inc., Ames, Iowa

[21] Appl. No.: 09/102,941

[22] Filed: Jun. 23, 1998

[51] Int. Cl.[7] .......................... A61K 31/19; A61K 31/195
[52] U.S. Cl. ............................ 514/557; 514/561; 514/565
[58] Field of Search ..................................... 514/557, 561, 514/565

[56] References Cited

U.S. PATENT DOCUMENTS

| | | |
|---|---|---|
| 4,992,470 | 2/1991 | Nissen . |
| 5,028,440 | 7/1991 | Nissen . |
| 5,348,979 | 9/1994 | Nissen et al. . |
| 5,360,613 | 11/1994 | Nissen . |
| 5,756,469 | 5/1998 | Beale . |

OTHER PUBLICATIONS

Met–Rx Substrate Technology, Inc., "Take Your Nutrition to New Levels of Performance with MET–Rx," *Product Advertisement* (©1997; believed to be available to public as early as 1996).

Met–Rx Substrate Technology, Inc., "MET–Rx Berry Medley," *Product Label* (©1998; believed to be available to public as early as 1996).

Met–Rx Substrate Technology, Inc., "KetoPro Ketogenic Nutrient Partitioning Formula," *Product Label* (©1999; believed to be available to public as early as 1996).

Met–Rx Substrate Technology, Inc., "We Know Your Sports Nutrition Customers," *Product Advertisement* (©1999; believed to be available to public as early as 1996).

Met–Rx Substrate Technology, Inc., "High Performance Series," *Product Advertisement* (believed to be available to public as earlly as 1996).

Met–Rx Substrate Technology, Inc., "MET–Rx High Performance Series Discover A Whole New Training Regimen!" *Product Advertisement* (believed to be available to public as early as 1996).

Met–Rx Substrate Technology, Inc., "What is HMB?" *Product Advertisement* (believed to be available to public as early as 1996).

Twinlab, "Anabolic/Anti–Catabolic Growth Fuel with HMB & Growth Potentiators," *Product Label* (believed to be available to public as early as 1996).

Twinlab, "Anti–Catabolic HMB Fuel Plus HMB, NAC, Glutamine & Creatine," *Product Label* (believed to be available to public as early as 1996).

Associated Press, "Disfiguring Fat Adds to Aids Misery," (1998), Article.

Barbul, Adrian, M.D., *Journal Parenteral and Enteral Nutrition* 10(2): 227–238 (1985).

Clark et al., "12th World AIDS Conference," (1998), Abstract.

Daly et al., *Surgery* 112(1):56–67 (1992).

Hammarqvist et al., "Amino Acids in Critical Care and Cancer," Chapter 3, pp. 27–44 (1994).

Metabolic Technologies, Inc. "MTI–AIDS NCMC001," (1998), Study outline.

Neu et al., *FASEB Journal* 10: 829–837 (1996).

Nissen et al., *J. Nutr. Biochem* 8: 300–311 (1997).

Nissen et al., *American Physiological Society* pp. 2095–2104 (1996).

Pichard et al., "AIDS," 12(1):53–63 (1998).

Sousa et al., *Nephron* 72:391–394 (1996).

Suttman et al., *J AM Diet Assoc.* 96(6):565–569 (1996).

Torosian, "Amino Acids in Critical Care and Cancer," Chapter 4, pp. 45–52 (1994).

*Primary Examiner*—Raymond Henley, III
*Attorney, Agent, or Firm*—Leydig, Voit & Mayer, Ltd.

[57] ABSTRACT

The present invention provides a composition comprising HMB and at least one amino acid. The present invention also provides a method for the treatment of disease-associated wasting of an animal, a method for decreasing the serum-level of triglycerides of an animal, a method for decreasing the serum viral load of an animal, and a method for redistributing fat in an animal having a visceral region and a subcutaneous region. All methods comprise administering to the animal a composition comprising HMB and at least one amino acid.

58 Claims, No Drawings

COMPOSITION COMPRISING β-HYDROXY-β-METHYLBUTYRIC ACID AND AT LEAST ONE AMINO ACID AND METHODS OF USE

TECHNICAL FIELD OF THE INVENTION

The present invention relates to a composition comprising β-hydroxy-β-methylbutyric acid and at least one amino acid, and methods of using the compositions to treat disease-associated wasting of an animal, to decrease the serum-level of triglycerides of an animal, to decrease the serum viral load of an animal, and to redistribute fat in an animal.

BACKGROUND OF THE INVENTION

The only product of leucine metabolism is ketoisocaproate (KIC). A minor product of KIC metabolism is β-hydroxy-β-methylbutyric acid (HMB).

HMB has been found to be useful within the context of a variety of applications. Specifically, in U.S. Pat. No. 5,360,613 (Nissen), HMB is described as useful for reducing blood levels of total cholesterol and low-density lipoprotein cholesterol. In U.S. Pat. No. 5,348,979 (Nissen et al.), HMB is described as useful for promoting nitrogen retention in humans. U.S. Pat. No. 5,028,440 (Nissen) discusses the usefulness of HMB to increase lean tissue development in meat-producing animals. Also, in U.S. Pat. No. 4,992,470 (Nissen), HMB is described as effective in enhancing the immune response of mammals.

While HMB has been previously described as useful for increasing the development of lean tissue mass in some animals, while decreasing the mass of fat, there has been no teaching or suggestion in the art that HMB is useful for increasing the lean tissue mass of an animal without decreasing the fat mass. Yet, under certain circumstances, it is desirable to increase the lean tissue mass of an animal without decreasing the fat mass of the animal. For example, one such circumstance is when an animal suffers from body tissue wasting as the result of disease, such as that associated with acquired immune deficiency syndrome (AIDS). Body tissue wasting can negatively impact the prognosis of humans with AIDS and can even hasten their disease-associated deterioration.

One method directed to body tissue wasting is described in U.S. Pat. No. 5,756,469 (Beale). The Beale patent discloses the use of a composition comprising pyruvate and/or a derivative thereof (e.g., pyruvyl amino acids) and a cortisol blocker to increase lean body mass of muscle tissue in a mammal and suggests that such a composition would be useful in the treatment of catabolic conditions associated with diseases such as cancer and AIDS. However, the Beale patent only evidences the efficacy of such a composition in increasing lean body tissue (by 15% as compared to control rats) in treated healthy rats, which gained 20% less fat than the control rats. As one of ordinary skill in the art would readily appreciate, the fact that a given composition is efficacious in a healthy organism does not necessarily mean that the same composition will be efficacious in a diseased organism suffering from a catabolic condition. In this regard, the Beale patent neither teaches nor suggests how a composition comprising HMB and at least one amino acid could be used to treat disease-associated wasting. Furthermore, the use of pyruvyl amino acids in the composition is disadvantageous because pyruvyl amino acids are costly and difficult to manufacture.

In view of the foregoing, there remains a need for a proven and cost-effective composition to treat disease-associated wasting. There also remains a need for a composition to decrease the serum-level of triglycerides of an animal, decrease the serum viral load of an animal, and redistribute fat in an animal. The present invention provides such a composition as well as methods of using such a composition to treat disease-associated wasting, decrease the serum-level of triglycerides of an animal, decrease the serum viral load of an animal, and redistribute fat in an animal.

BRIEF SUMMARY OF THE INVENTION

The present invention provides a composition comprising HMB and at least one amino acid. The present invention also provides a method for the treatment of disease-associated wasting of an animal, a method for decreasing the serum-level of triglycerides of an animal, a method for decreasing the serum viral load of an animal, and a method for redistributing fat in an animal having a visceral region and a subcutaneous region. All methods comprise administering to the animal a composition comprising HMB and at least one amino acid.

DETAILED DESCRIPTION OF THE INVENTION

It has now been surprisingly and unexpectedly discovered that, unlike HMB alone, a composition comprising HMB and at least one amino acid can increase lean tissue mass without a concomitant decrease in fat mass. Moreover, in contrast to HMB alone, no aerobic exercise is required to realize such an increase in lean tissue mass when the composition is administered to animals suffering from disease-associated wasting. As the examples below illustrate, the efficacy of the composition in increasing lean tissue mass without decreasing fat mass is enhanced when the animal is suffering from disease-associated wasting.

Additionally, the present inventive composition is surprisingly useful for decreasing the serum-level of triglycerides of animals and decreasing the serum viral load of animals. The present composition is also surprisingly useful for redistributing fat from the visceral region of an animal to the subcutaneous region of the animal. That the present composition is useful for such a purpose is especially surprising in light of the fact that it has been observed that HMB alone causes a shift from subcutaneous fat stores to visceral fat stores (e.g., intramuscular fat stores). While not wishing to be bound to any particular theory, it appears that all of the foregoing are attributable to a synergistic effect between the HMB and the at least one amino acid in the present inventive composition.

In view of the above, in one embodiment, the present invention provides a composition comprising HMB and at least one amino acid.

HMB, which is also referred to as β-hydroxy-β-methylbutyric acid, or β-hydroxy-isovalaryic acid, can be represented in its free acid form as $(CH_3)_2(OH)CCH_2COOH$. The term "HMB" refers to the compound having the foregoing chemical formula, in both its free acid and salt forms, and derivatives thereof. While any suitable form of HMB can be used within the context of the present invention, preferably, HMB is selected from the group consisting of a free acid, a salt, an ester, and a lactone; more preferably, HMB is a salt.

While any pharmaceutically suitable salt of HMB can be used within the context of the present invention, preferably, the HMB salt is water-soluble or becomes water-soluble in the stomach or intestines of an animal. More preferably, the HMB salt is selected from the group consisting of a sodium salt, a potassium salt, a magnesium salt, a chromium salt, and a calcium salt. Most preferably, the HMB salt is a calcium salt. However, other non-toxic salts, such as other alkali metal or alkaline earth metal salts, can be used. When HMB is to be administered in an edible form, it is preferred that the salt be dry, non-sticky, and finely-divided for blending with other foodstuffs.

Similarly, any pharmaceutically acceptable ester can be used in the context of the present invention. Desirably, the HMB ester is rapidly converted to HMB in its free acid form. Preferably, the HMB ester is a methyl ester or ethyl ester. HMB methyl ester and HMB ethyl ester are rapidly converted to the free acid form of HMB.

Likewise, any pharmaceutically acceptable lactone can be used in the context of the present invention. Desirably, the HMB lactone is rapidly converted to HMB in its free acid form. Preferably, the HMB lactone is an isovalaryl lactone or a similar lactone. Such lactones are rapidly converted to the free acid form of HMB.

Methods for producing HMB and its derivatives are well-known in the art. For example, HMB can be synthesized by oxidation of diacetone alcohol. One suitable procedure is described by Coffman et al., *J. Am. Chem. Soc.* 80: 2882–2887 (1958). As described therein, HMB is synthesized by an alkaline sodium hypochlorite oxidation of diacetone alcohol. The product is recovered in free acid form, which can be converted to the desired salt. For example, HMB can be prepared as its calcium salt by a procedure similar to that of Coffman et al. in which the free acid of HMB is neutralized with calcium hydroxide and recovered by crystallization from an aqueous ethanol solution. The calcium salt of HMB is commercially available from Metabolic Technologies, Ames, Iowa.

As defined herein, the term "amino acid" means any naturally occurring or synthetically derived amino acid except pyruvyl amino acids, which are costly and difficult to manufacture. Synthetically derived, or unnatural amino acids, and methods for making them are well-known in the art and are disclosed in, for example, U.S. Pat. No. 5,710, 249 (Hoeger et al.). The at least one amino acid can be any pharmaceutically acceptable amino acid. Desirably, the at least one amino acid is one that, when administered with HMB, will result in an increase in the total body weight of an animal suffering from disease-associated wasting, result in a decrease in the serum-level of triglycerides of an animal, result in a decrease in the serum viral load of an animal, or result in the redistribution of the fat of an animal. Preferably, the amino acid is the L-isomer of a natural amino acid. More preferably, the amino acid is selected from the group consisting of L-arginine, L-glutamine, L-lysine, L-leucine, L-isoleucine, L-valine, L-methionine, L-cysteine, glycine and combinations thereof. Most preferably, the amino acid is the combination of L-arginine and L-glutamine.

The present inventive composition can be in any pharmaceutically acceptable form. Pharmaceutically acceptable forms include, but are not limited to, solids, such as tablets or capsules, and liquids, such as intravenous solutions. Also, the composition can be administered utilizing any pharmaceutically acceptable carrier. Pharmaceutically acceptable carriers are well known in the art and examples of such carriers include various starches and saline solutions.

Preferably, the present inventive composition comprises HMB in the form of its calcium salt, L-arginine and L-glutamine. Preferably, a composition in accordance with the present invention comprises HMB in an amount from about 0.5 g to about 30 g and at least one amino acid in an amount from about 1 g to about 100 g.

In view of the above, the present invention provides, in another embodiment, a method for the treatment of the disease-associated wasting of an animal, such as a mammal, preferably a human. The method comprises administering to the animal the above-described composition, which comprises HMB and at least one amino acid, in amounts sufficient to treat the disease-associated wasting, wherein, upon administration of the composition to the animal, the disease-associated wasting is treated.

The amounts of HMB and the at least one amino acid that are sufficient to treat disease-associated wasting in a given animal can be determined in accordance with methods well-known in the art. When treating the disease-associated wasting of an animal, desirably, the composition comprising HMB and the at least one amino acid is administered to an animal suffering from disease-associated wasting in such an amount, in such a manner, and over such a period of time that the animal's lean tissue mass will increase without a concomitant decrease in the animal's fat mass. Preferably, HMB and the at least one amino acid are present in the composition in relative amounts such that the animal's lean tissue mass will increase by at least about 10 g per day over the period of time of administration, more preferably, by at least about 30 g per day over the period of time of administration, and, most preferably, by at least about 40 g per day over the period of time of administration. It is also desirable that the amount of the at least one amino acid is greater than the amount of HMB. Preferably, the amount of the at least one amino acid is at least four times greater than the amount of HMB. As an example, within the context of treating the AIDS-associated wasting of a human, when the composition is orally administered about twice a day for about eight weeks, the composition preferably comprises from about 0.5 g to about 50 g of L-arginine, from about 0.5 g to about 50 g of L-glutamine, and from about 0.5 g to about 30 g of the calcium salt of HMB, more preferably, from about 1 g to about 30 g of L-arginine, from about 1 g to about 30 g of L-glutamine, and from about 0.5 g to about 20 g of the calcium salt of HMB, and, most preferably, from about 2 g to about 20 g of L-arginine, from about 2 g to about 20 g of L-glutamine, and from about 0.5 g to about 10 g of the calcium salt of HMB.

In yet another embodiment, the present invention provides a method of decreasing the serum-level of triglycerides of an animal, such as a mammal, preferably a human, in need thereof. Preferably, the need of the animal to have its serum-level of triglycerides decreased arises from a disease that causes wasting of the animal. The method comprises administering to the animal the above-described composition, which comprises HMB and at least one amino acid, in amounts sufficient to decrease the serum-level of triglycerides of the animal, wherein upon administration of the composition to the animal, the serum-level of triglycerides of said animal is decreased.

The amounts of HMB and the at least one amino acid that are sufficient to decrease the serum-level of triglycerides of the animal can be determined in accordance with methods well-known in the art. Desirably, the composition, comprising HMB and at least one amino acid, is administered to an animal in need of a decrease in its serum-level of triglycerides in such an amount, in such a manner, and over such a period of time that the animal's serum-level of triglycerides decreases. Preferably, HMB and the at least one amino acid are present in the composition in relative amounts such that the animal's serum-level of triglycerides is decreased by at least about 2% over the period of time of administration, more preferably, by at least about 5% over the period of time of administration, and, most preferably, by at least about 10% over the period of time of administration. It is also desirable that the amount of the at least one amino acid is greater than the amount of HMB. Preferably, the amount of the at least one amino acid is at least four times greater than the amount of HMB. As an example, within the context of decreasing the serum-level of triglycerides of a human, when the composition is orally administered about twice a day for about eight weeks, the composition preferably comprises from about 0.5 g to about 50 g of L-arginine, from about 0.5 g to about 50 g of L-glutamine, and from about 0.5 g to about 30 g of the calcium salt of HMI, more preferably, from about 1 g to about 30 g of L-arginine, from about 1 g to about 30 g of L-glutamine, and from about 0.5 g to about 20 g of the calcium salt of HMB, and, most preferably, from about 2 g to about 20 g of L-arginine, from about 2 g to about 20 g of L-glutamine, and from about 0.5 g to about 10 g of the calcium salt of HMB.

Another embodiment of the present invention is directed to a method of decreasing the serum viral load of an animal, such as a mammal, preferably a human, in need thereof. Preferably, the need of the animal to have its serum viral load decreased arises from a disease that causes wasting of the animal. The method comprises administering to the animal the above-described composition, which comprises HMB and at least one amino acid, in amounts sufficient to decrease the serum viral load of the animal, wherein, upon administration of the composition to the animal, the serum viral load of said animal is decreased.

The amounts of HMB and the at least one amino acid that are sufficient to decrease the serum viral load of the animal can be determined in accordance with methods well-known in the art. Desirably, the composition, comprising HMB and at least one amino acid, is administered to an animal in need of a decrease in its serum viral load in such an amount, in such a manner, and over such a period of time that the animal's serum viral load decreases. Preferably, HMB and the at least one amino acid are present in the composition in relative amounts such that the animal's serum viral load (as characterized by the equation $\log_{10}$-change in viral load) is decreased by at least about 0.1 over the period of time of administration, more preferably, by at least about 0.2 over the period of time of administration, and, most preferably, by at least about 0.3 over the period of time of administration. It is also desirable that the amount of the at least one amino acid is greater than the amount of HMB. Preferably, the amount of the at least one amino acid is at least four times greater than the amount of HMB. As an example, within the context of decreasing the serum viral load of a human in need thereof, when the composition is orally administered about twice a day for about eight weeks, the composition preferably comprises from about 0.5 g to about 50 g of L-arginine, from about 0.5 g to about 50 g of L-glutamine, and from about 0.5 g to about 30 g of the calcium salt of HMB, more preferably, from about 1 g to about 30 g of L-arginine, from about 1 g to about 30 g of L-glutamine, and from about 0.5 g to about 20 g of the calcium salt of HMB, and, most preferably, from about 2 g to about 20 g of L-arginine, from about 2 g to about 20 g of L-glutamine, and from about 0.5 g to about 10 g of the calcium salt of HMB.

In yet another embodiment, the present invention provides a method of redistributing fat in an animal, such as a mammal, preferably a human, in need thereof. Preferably, the need of the animal to have its fat redistributed arises from a disease that causes wasting of the animal. The method comprises administering to an animal having a visceral region and a subcutaneous region the above-described composition, which comprises HMB and at least one amino acid, in amounts sufficient to redistribute fat from the visceral region of the animal to the subcutaneous region of the animal, wherein, upon administration of the composition to the animal, the fat from the visceral region of the animal is redistributed to the subcutaneous region of the animal.

The amounts of HMB and the at least one amino acid that are sufficient to redistribute fat from the animal's visceral region to the animal's subcutaneous region can be determined in accordance with methods well-known in the art. Desirably, the composition, comprising HMB and at least one amino acid, is administered to an animal in need of a redistribution of fat in such an amount, in such a manner, and over such a period of time that the animal's fat redistributes from its visceral region to its subcutaneous region. Preferably, HMB and the at least one amino acid are present in the composition in relative amounts so that fat from the animal's visceral region is redistributed to its subcutaneous region such that the amount of fat in the animal's subcutaneous region increases by at least about 0.5% over the period of time of administration, more preferably, by at least about 2% over the period of time of administration, and, most preferably, by at least about 3% over the period of time of administration. It is also desirable that the amount of the at least one amino acid is greater than the amount of HMB. Preferably, the amount of the at least one amino acid is at least 4 times greater than the amount of HMB. As an example, within the context of redistributing fat from the visceral region to the subcutaneous region of a human, when the composition is orally administered about twice a day for about eight weeks, the composition preferably comprises from about 0.5 g to about 50 g of L-arginine, from about 0.5 g to about 50 g of L-glutamine, and from about 0.5 g to about 30 g of the calcium salt of HMB, more preferably, from about 1 g to about 30 g of L-arginine, from about 1 g to about 30 g of L-glutamine, and from about 0.5 g to about 20 g of the calcium salt of HMB, and, most preferably, from about 2 g to about 20 g of L-arginine, from about 2 g to about 20 g of L-glutamine, and from about 0.5 g to about 10 g of the calcium salt of HMB.

Any disease with which wasting is associated can be treated with the present composition and in accordance with the present methods. Preferably, the disease is selected from the group consisting of cancer, chronic pulmonary disease, age-associated wasting, chronic kidney disease, wasting associated with long-term hospitalization that restricts the animal's mobility, and AIDS. More preferably, the disease is AIDS.

The composition comprising HMB and at least one amino acid can be administered to an animal in the context of the present inventive methods in any suitable manner. Preferably, the composition is administered either in an edible form or intravenously.

When the composition is administered orally in an edible form, the composition is preferably in the form of a foodstuff or a pharmaceutical medium, more preferably, in the form of a foodstuff. Any suitable foodstuff comprising the composition can be utilized within the context of the present invention. In order to prepare the composition as a foodstuff, the composition will normally be blended with the appropriate foodstuff in such a way that the composition is substantially uniformly distributed in the foodstuff. Alternatively, the composition can be dissolved in a liquid, such as water. Although any suitable pharmaceutical medium comprising the composition can be utilized within the context of the present invention, preferably, the composition is blended with a suitable pharmaceutical carrier, such as dextrose or sucrose, and is subsequently tabulated or encapsulated as described above.

When an HMB salt is orally administered in its edible form to a ruminant, the HMB salt is not subject to significant rumen destruction. Following oral administration, the HMB salt appears to pass intact through the rumen into the intestines of the ruminant where it is absorbed and distributed into the circulatory system.

Furthermore, the composition can be intravenously administered in any suitable manner. For administration via intravenous infusion, the composition is preferably in a water-soluble non-toxic form. Intravenous administration is particularly suitable for hospitalized patients that are undergoing intravenous (IV) therapy. For example, the composition can be dissolved in an IV solution (e.g., a saline or glucose solution) being administered to the patient. Also, the composition can be added to nutritional IV solutions, which may include other amino acids and/or lipids. The amounts of the composition to be administered intravenously can be similar to levels used in oral administration, but it is believed that maximized retention should be obtainable at lesser doses by infusion. Advantages to intravenous infusion over oral administration include the fact that administration via intravenous infusion is more controlled and accurate.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period or, alternatively, multiple doses can be administered over an eight week time period).

EXAMPLES

The following examples further illustrate the invention but, of course, should not be construed as in any way limiting its scope.

Example 1

This example demonstrates how the present inventive composition increased lean tissue mass without decreasing fat mass in healthy humans, irrespective of exercise, and reduces serum-level of triglycerides.

Prior to a study on the effects of the HMB/arginine/glutamine composition (JUVEN) in AIDS patients, 40 HIV-negative men were assigned to either a placebo or a JUVEN group. During the four-week study, half of the subjects in each group underwent an exercise program, while the other half continued a sedentary lifestyle. Each subject in the JUVEN group received a treatment comprising 14 g of arginine (free base), 14 g of glutamine, and 3 g of the calcium salt of HMB each day for four-weeks. Each group received its supplementation in a foil packet, given in two equal doses each day. Body composition (e.g., underwater weight) and strength, as demonstrated by bench pressing, were measured before the beginning of the study and at the end of the study. Blood was drawn prior to the experiment and at 2 and 4 weeks for chemscreens. The results of the study are summarized in Table 1 below.

TABLE 1

Relative Change of JUVEN Mixture Compared To Placebo In HIV-Negative Humans

| Net change | $p <$ | Variable | Interpretation and/or comparison with HMB supplementation alone |
|---|---|---|---|
| 3% | 0.29 | Glucose | No change consistent with HMB alone |
| −12% | 0.05 | Uric Acid | Decrease not seen with HMB alone |
| 22% | 0.01 | Blood urea | Increase due to increased nitrogen intake with supplement |
| 3% | 0.25 | Creatinine, Serum | No change consistent with HMB alone |
| 2% | 0.22 | Protein | No change consistent with HMB alone |
| 2% | 0.16 | Albumin | Slight increase consistent with HMB increase alone |
| 2% | 0.55 | Globulin | Slight increase consistent with HMB increase alone |
| −9% | 0.38 | Bilirubin | No change consistent with HMB alone |
| −6% | 0.15 | Alkaline Phosphatase | No change consistent with HMB alone |
| −9% | 0.67 | Creatine Phospho Kinase | Decrease consistent with HMB decrease alone |
| −3% | 0.49 | LDH | No change consistent with HMB alone |
| −2% | 0.87 | SGOT | No change consistent with HMB alone |
| −17% | 0.20 | SGPT | No change consistent with HMB alone |
| −1% | 0.95 | GGT | No change consistent with HMB alone |
| −12% | 0.38 | Iron | No change consistent with HMB alone |
| 1% | 0.83 | Cholesterol, Total | No change in contrast to decrease with HMB alone |
| −15% | 0.22 | Triglycerides | No change consistent with HMB alone |
| 13% | 0.01 | High density cholesterol | Increase greater than with HMB alone |
| −15% | 0.24 | VLDL Chol | No change consistent with HMB alone |
| 3% | 0.52 | Low Density cholesterol (LDL) | No change in contrast to an aver7% decrease with HMB alone |
| −8% | 0.18 | Coronary disease risk | Decrease consistent with that of HBM alone |
| −7% | 0.18 | LDL/HDL Ratio | Decrease consistent with that of HBM alone |
| −4% | 0.76 | #CD3 | Limited comparative data on HMB alone |
| −1% | 0.93 | #CD4 | Limited comparative data on HMB alone |
| −14% | 0.27 | #CDB | Limited comparative data on HMB alone |
| 7% | 0.27 | Total White cell count | No change consistent with HMB alone |
| 2% | 0.07 | Total Red call count | Increase not seen with HMB alone |
| 2% | 0.10 | Hemoglobin | Increase not seen with HMB alone |
| 6% | 0.15 | Hematocrit | Increase not seen with HMB alone |
| 11% | 0.31 | Number of neutrophils | No change consistent with HMB alone |
| 5% | 0.44 | Number of lymphocytes | No change consistent with HMB alone |
| 0.05 kg (plac.) and 0.01 kg (JUVEN) | 0.90 | Fat Mass Under Water | Nonsignificant change-however consistent with HMB alone |
| 0.83 kg | 0.78 | Lean Mass Under Water | Nonsignificant change- |

TABLE 1-continued

Relative Change of JUVEN Mixture Compared To Placebo In HIV-Negative Humans

| Net change | p < . | Variable | Interpretation and/or comparison with HMB supplementation alone |
|---|---|---|---|
| (plac.) and 0.98 kg (JVVEN) | | | however consistent with HMB alone |
| −3% | 0.32 | Systolic Blood Pressure | Nonsignificant change- however consistent with HMB alone |
| −5% | 0.38 | Diastolic Blood Pressure | Nonsignificant change- however consistent with HMB alone |

The results of the foregoing study indicate that administration of JUVEN to HIV-negative humans caused a 1 kg increase in total body weight (approximately 0.98 kg of lean tissue mass and approximately 0.01 kg of fat mass). Approximately 0.88 kg of an increase in total body weight (approximately 0.83 kg of lean tissue mass and approximately 0.05 kg of fat mass) was observed in the placebo group. Accordingly, the JUVEN-treated group realized a 12.5% increase in total body weight over the placebo group, irrespective of exercise. In addition, the serum-level of triglycerides in the JUVEN group was decreased by 15% relative to the placebo group.

Example 2

This example demonstrates how the present inventive composition decreases the serum-level of triglycerides and serum viral load, and increases total body weight (lean tissue mass and fat mass), without a concomitant decrease in fat mass, in AIDS patients.

A study was initiated at a hospital to examine the safety and efficacy of the JUVEN composition in altering the course of wasting in patients with established HIV infections and AIDS. The HIV infections were confirmed from hospital records and the patients were diagnosed with AIDS based upon standard CDC criteria. Subjects and/or personnel involved in the study did not know whether they were assigned to the placebo group or to the test group, i.e., the group treated with the JUVEN composition.

Twenty-one subjects were assigned to the placebo group, wherein each subject received bulk maltodextrin for eight weeks. Similarly, twenty-three subjects were assigned to the test group, wherein each subject received a treatment comprising 14 g of arginine (free-base), 14 g glutamine, and 3 g of the calcium salt of HMB each day for eight weeks (JUVEN). Each group received its supplementation in a foil packet, given in two equal doses each day. Each dose was supplied in a separate packet and was allocated by subject number. Every week for eight weeks, subjects reported to the medical center to pick up a one-week allotment of the supplement assigned to them, provide a body weight (fasted), record vital signs, and fill out the experimental questionnaires.

Blood sampling occurred prior to the beginning of the study and after 2, 4, 6, and 8 weeks for blood chemistry, liver function tests, blood lipids and hematology determinations (Lab Corp., New Jersey). Additional blood was sampled prior to the beginning of the study and after 4 and 8 weeks for $CD4^+$ counts (Lab Corp.) and prior to the beginning of the study and after 8 weeks for HIV viral load measurements (Lab Corp.). Compliance to the protocol was indicated by an additional sample taken at 0, 2, 4, 6, and 8 weeks in which blood-HMB levels were measured.

Body composition was assessed using four methods. Changes in lean body mass and fat mass were determined by skin-fold thickness and air displacement plethysmography (Bod-Pod®, LMI, California) prior to the beginning of the study and after 4 and 8 weeks. Circumferences of the forearm, upper arm and thigh were determined prior to the beginning of the study and after 4 and 8 weeks. The results of the blood-work are summarized in Table 2 below. Table 3, below, summarizes the results of the study with respect to lean tissue mass and fat mass gains.

TABLE 2

Partial Summary Of Changes In Serum Chemistry And Hematology Of AIDS Patients

| Parameter | % change due to JUVEN | Significance | Effect in Normal (see Table 2 below) |
|---|---|---|---|
| Glucose | 17% | .34 | 3% |
| BUN | 39% | .01 | 22% |
| Potassium | −3.5% | .07 | −7 |
| Uric acid | −19% | .55 | −12% |
| Triglycerides (4 wk) | −20% | .20 | −15% |
| Total Bilirubin | 16% | .17 | −9% |
| Eosinophil | 20% | .29 | −2% |
| Lymph (abs) | 29% | .03 | 5% |
| CD3 (abs) | 25% | .02 | −4% |
| CD8 (abs) | 26% | .02 | −17% |
| CD4 (abs) | 30% | .22 | −1% |
| Hb | 4% | .22 | 2% |
| Viral Load ($log_{10}$- change in viral load) | 0.40 (plac.) −0.32 (JUVEN) | 0.01 | — |

TABLE 3

Partial Summary Of Changes In Lean Tissue Mass and Fat Mass Of AIDS Patients

| Parameter | Placebo Change | JUVEN Change | Significance |
|---|---|---|---|
| Lean Gain (Bod-Pod) (kg per 8 weeks) | −0.7 kg | 2.55 kg | .01 |
| Fat gain (Bod Pod) (kg per 8 weeks) | 1.07 kg | 0.43 kg | .7 |
| Lean Gain (Skin-fold thickness) (kg per 8 weeks) | 0.10 kg | 1.6 kg | .05 |
| Fat Gain (Skin-fold thickness) (kg per 8 weeks) | 0.17 kg | 1.4 kg | .16 |

As Table 2 indicates, with respect to humans suffering from AIDS, the JUVEN group experienced a 20% decrease in its serum-level of triglycerides with respect to the placebo group. Also, the serum viral load (as characterized by the equation $log_{10}$-change in viral load) of the JUVEN group decreased by 0.32, while the placebo group experienced a viral load increase of 0.40.

As Table 3 indicates, the JUVEN group gained approximately 3 kg of total body weight (approximately 2.55 kg or approximately 1.6 kg of lean tissue mass as determined by Bod-Pod and skin-fold thickness measurements, respectively, and approximately 0.43 kg or 1.4 kg of fat mass as determined by Bod-Pod and skin-fold thickness measurements, respectively.). In contrast, the placebo group gained approximately 0.3 kg of total body weight. While the total body weight increase was the same for both the Bod-Pod and skin-fold thickness (measures subcutaneous mass) measurements, the differences between the measurements is likely a result of fat redistribution from the visceral region to the subcutaneous region of the subject (see Example 3 below).

Upon administration of JUVEN, the patients suffering from AIDS gained approximately 3.0 kg of total body weight, whereas the HIV-negative patients (Example 1) gained approximately 1.0 kg. Therefore, the present inventive composition surprisingly and unexpectedly effected a greater increase in total body weight in AIDS patients, who suffer from disease-associated wasting, than in HIV-negative patients, who were not suffering from disease-associated wasting.

Example 3

This example demonstrates how the present inventive composition redistributes fat from the visceral region to the subcutaneous region of a human.

The study was carried out on HIV-negative patients as described in Example 1, above, and on AIDS patients as described in Example 2, above. Total body fat was measured by the Bod-Pod, which estimates total body fat based on body density. Subcutaneous body fat was measured by measuring the thickness of a pinch of skin in seven areas of the body (i.e., chest, axilla, triceps, subscapular, supra iliac, abdominal, and thigh). The results of the seven subcutaneous fat measurements were then summed. All measurements were taken before the study began and at the end of the 8-week study. The results of the measurements are summarized in Table 4 below.

TABLE 4

Redistribution Of Fat From Visceral Region To Subcutaneous Region In Both HIV-Negative Patients And AIDS Patients

| Parameter | Placebo Change | JUVEN Change | Significance |
|---|---|---|---|
| Lean Gain (Bod- AIDS patients (Bod Pod) (kg per 8 weeks) | −0.7 kg | 2.55 kg | .01 |
| Fat Gain in AIDS patients (Bod Pod) (kg per 8 weeks) | 1.07 kg | 0.43 kg | .7 |
| Subcutaneous Fat in AIDS patients (skin-fold thickness) (sum of 7 areas) (mm of change) | 3.04 mm | 9.50 mm | .35 |
| Subcutaneous Fat in HIV-Negative patients (skin-fold thickness) (sum of 7 areas) (mm of change) | 2.4 mm | 8.7 mm | .05 |
| Estimated fat redistribution to the subcutaneous region in AIDS patients (kg) | −0.80 kg | 1.0 kg | — |

As Table 4 indicates, the placebo group of AIDS patients increased its subcutaneous fat by approximately 3.04 mm while the JUVEN group of AIDS patients increased its subcutaneous fat by approximately 9.5 mm. Thus, the gain in subcutaneous fat in AIDS patients was 3-fold more in the JUVEN group than in the placebo group, while the total body fat gained in the JUVEN group was only half that of the placebo group (0.43 kg of total body fat for the JUVEN group compared with 1.07 kg of total body fat for the placebo group). Therefore, administration of JUVEN resulted in redistribution of fat from the visceral region of the human to the subcutaneous region of the human.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A composition comprising from about 0.5 g to about 30 g of β-hydroxy-β-methylbutyric acid (HMB), wherein said from about 0.5 g to about 30 g is based on the weight of the calcium salt of HMB, from about 0.5 g to about 50 g of L-arginine, and from about 0.5 g to about 50 g of L-glutamine.

2. The composition of claim 1, which comprises from about 0.5 g to about 20 g of HMB, wherein said from about 0.5 g to about 20 g is based on the weight of the calcium salt of HMB, from about 1 g to about 30 g of L-arginine, and from about 1 g to about 30 g of L-glutamine.

3. The composition of claim 2, which comprises from about 0.5 g to about 10 g of HMB, wherein said from about 0.5 g to about 10 g is based on the weight of the calcium salt of HMB, from about 2 g to about 20 g of L-arginine, and from about 2 g to about 20 g of L-glutamine.

4. A method for the treatment of disease-associated wasting of an animal, which method comprises administering to said animal a composition comprising HMB and at least one amino acid in amounts sufficient to treat said disease-associated wasting, wherein, upon administration of the composition to the animal, said disease-associated wasting is treated.

5. The method of claim 4, wherein said HMB is in a form selected from the group consisting of a free acid, a salt, an ester, and a lactone.

6. The method of claim 5, wherein said HMB is in the form of a salt.

7. The method of claim 6, wherein said HMB is in the form of a salt selected from the group consisting of a sodium salt, a potassium salt, a magnesium salt, a chromium salt, and a calcium salt.

8. The method of claim 7, wherein said HMB is in the form of a calcium salt.

9. The method of claim 5, wherein said HMB is in the form of an ester.

10. The method of claim 9, wherein said HMB is in the form of an ester selected from the group consisting of a methyl ester and an ethyl ester.

11. The method of claim 6, wherein said HMB is in the form of a lactone.

12. The method of claim 11, wherein said HMB is in the form of an isovalaryl lactone.

13. The method of claim 4, wherein said at least one amino acid is selected from the group consisting of L-arginine, L-glutamine, L-lysine, L-leucine, L-isoleucine, L-valine, L-methionine, L-cysteine, glycine, and combinations thereof.

14. The method of claim 13, wherein said at least one amino acid is the combination of L-arginine and L-glutamine.

15. The method of claim 14, wherein said HMB is in the form of a calcium salt and said at least one amino acid is the combination of L-arginine and L-glutamine.

16. The method of claim 14, wherein said HMB and said at least one amino acid are present in amounts sufficient to increase the lean tissue mass of said animal by at least 10 g per day.

17. The method of claim 4, wherein said HMB is present in an amount from about 0.5 g to about 30 g and said amount of at least one amino acid is present in an amount from about 1 g to about 100 g.

18. The method of claim 4, wherein said disease-associated wasting is that which is associated with cancer, chronic pulmonary disease, age, chronic kidney disease, long-term hospitalization that restricts the animal's mobility, or AIDS.

19. The method of claim 18, wherein said disease-associated wasting is associated with AIDS.

20. The method of claim 4, wherein said composition comprises from about 0.5 g to about 30 g of HMB, wherein said from about 0.5 g to about 30 g is based on the weight of the calcium salt of HMB, from about 0.5 g to about 50 g of L-arginine, and from about 0.5 g to about 50 g of L-glutamine.

21. The method of claim 20, wherein said composition comprises from about 0.5 g to about 20 g of HMB, wherein said from about 0.5 g to about 20 g is based on the weight of the calcium salt of HMB, from about 1 g to about 30 g of L-arginine, and from about 1 g to about 30 g of L-glutamine.

22. The method of claim 21, wherein said composition comprises from about 0.5 g to about 10 g of HMB, wherein said from about 0.5 g to about 10 g is based on the weight of the calcium salt of HMB, from about 2 g to about 20 g of L-arginine, and from about 2 g to about 20 g of L-glutamine.

23. A method for decreasing the serum-level of triglycerides of an animal, which method comprises administering to said animal a composition comprising HMB and at least one amino acid in amounts sufficient to decrease the serum-level of triglycerides of said animal, wherein, upon administration of the composition to the animal, the serum-level of triglycerides of said animal is decreased.

24. The method of claim 23, wherein said HMB is in a form selected from the group consisting of a free acid, a salt, an ester, and a lactone.

25. The method of claim 24, wherein said HMB is in the form of a salt.

26. The method of claim 25, wherein said HMB is in the form of a salt selected from the group consisting of a sodium salt, a potassium salt, a magnesium salt, a chromium salt, and a calcium salt.

27. The method of claim 26, wherein said HMB is in the form of a calcium salt.

28. The method of claim 24, wherein said HMB is in the form of an ester.

29. The method of claim 28, wherein said HMB is in the form of an ester selected from the group consisting of a methyl ester and an ethyl ester.

30. The method of claim 24, wherein said HMB is in the form of a lactone.

31. The method of claim 30, wherein said HMB is in the form of an isovaleryl lactone.

32. The method of claim 23, wherein said at least one amino acid is selected from the group consisting of L-arginine, L-glutamine, L-lysine, L-leucine, L-isoleucine, L-valine, L-methionine, L-cysteine, glycine, and combinations thereof.

33. The method of claim 32, wherein said at least one amino acid is the combination of L-arginine and L-glutamine.

34. The method of claim 23, wherein said HMB is in the form of a calcium salt and said at least one amino acid is the combination of L-arginine and L-glutamine.

35. A method for decreasing the serum viral load of an animal, which method comprises administering to said animal a composition comprising HMB and at least one amino acid in amounts sufficient to decrease the serum viral load of said animal, wherein, upon administration of the composition to the animal, the serum viral load of said animal is decreased.

36. The method of claim 31, wherein said HMB is in a form selected from the group consisting of a free acid, a salt, an ester, and a lactone.

37. The method of claim 36, wherein said HMB is in the form of a salt.

38. The method of claim 37, wherein said HMB is in the form of a salt selected from the group consisting of a sodium salt, a potassium salt, a magnesium salt, a chromium salt, and a calcium salt.

39. The method of claim 38, wherein said HMB is in the form of a calcium salt.

40. The method of claim 36, wherein said HMB is in the form of an ester.

41. The method of claim 40, wherein said HMB is in the form of an ester selected from the group consisting of a methyl ester and an ethyl ester.

42. The method of claim 36, wherein said HMB is in the form of a lactone.

43. The method of claim 42, wherein said HMB is in the form of an isovaleryl lactone.

44. The method of claim 35, wherein said at least one amino acid is selected from the group consisting of L-arginine, L-glutamine, L-lysine, L-leucine, L-isoleucine, L-valine, L-methionine, L-cysteine, glycine, and combinations thereof.

45. The method of claim 44, wherein said at least one amino acid is the combination of L-arginine and L-glutamine.

46. The method of claim 35, wherein said HMB is in the form of a calcium salt and said at least one amino acid is the combination of L-arginine and L-glutamine.

47. A method for redistributing fat in an animal having a visceral region and a subcutaneous region, which method comprises administering to said animal a composition comprising HMB and at least one amino acid in amounts sufficient to redistribute fat from the visceral region of said animal to the subcutaneous region of said animal, wherein, upon administration of the composition to the animal, the fat from the visceral region of said animal is redistributed to the subcutaneous region of said animal.

48. The method of claim 47, wherein said HMB is in a form selected from the group consisting of a free acid, a salt, an ester, and a lactone.

49. The method of claim 48, wherein said HMB is in the form of a salt.

50. The method of claim 49, wherein said HMB is in the form of a salt selected from the group consisting of a sodium salt, a potassium salt, a magnesium salt, a chromium salt, and a calcium salt.

51. The method of claim 50, wherein said HMB is in the form of a calcium salt.

52. The method of claim 48, wherein said HMB is in the form of an ester.

53. The method of claim 52, wherein said HMB is in the form of an ester selected from the group consisting of a methyl ester and an ethyl ester.

54. The method of claim 48, wherein said HMB is in the form of a lactone.

55. The method of claim 54, wherein said HMB is in the form of an isovalaryl lactone.

56. The method of claim 47, wherein said at least one amino acid is selected from the group consisting of L-arginine, L-glutamine, L-lysine, L-leucine, L-isoleucine, L-valine, L-methionine, L-cysteine, glycine, and combinations thereof.

57. The method of claim 56, wherein said at least one amino acid is the combination of L-arginine and L-glutamine.

58. The method of claim 47, wherein said HMB is in the form of a calcium salt and said at least one amino acid is the combination of L-arginine and L-glutamine.

* * * * *

UNITED STATES PATENT AND TRADEMARK OFFICE
CERTIFICATE OF CORRECTION

PATENT NO.    : 6,031,000
DATED         : February 29, 2000
INVENTOR(S)   : Steven L. Nissen; Naji M. Abumrad It is certified that error appears in the above-identified patent and that said Letters Patent is hereby corrected as shown below:

Column 2,
Lines 54-55, "(CH3)2(OH)CCH2COOH" should read -- $(CH_3)_2(OH)CCH_2COOH$ --

Column 5,
Line 12, "HMI" should read -- HMB --

Column 8, Table 1,
Row 9, "-6%" should read -- 6% --
Row 25, "#CDB" should read -- #CD8 --

Column 9,
Line 21, "0.98 kg 5 of" should read -- 0.98 kg of --

Column 11, Table 4,
Row 1, "(Bod-" should read -- in --

Column 12, claim 11,
Line 62, "claim 6" should read -- claim 5 --

Column 13, claim 15,
Line 7, "claim 14" should read -- claim 4 --

Column 13, claim 16,
Line 10, "claim 14" should read -- claim 4 --

Column 14, claim 36,
Line 19, "claim 31" should read -- claim 35 --

Signed and Sealed this

Twenty-fifth Day of December, 2001

*Attest:*

*Attesting Officer*

JAMES E. ROGAN
*Director of the United States Patent and Trademark Office*